(12) United States Patent
Burlon et al.

(10) Patent No.: US 9,305,354 B2
(45) Date of Patent: Apr. 5, 2016

(54) APPARATUS AND METHOD FOR MAPPING A THREE-DIMENSIONAL SPACE IN MEDICAL APPLICATIONS FOR DIAGNOSTIC, SURGICAL OR INTERVENTIONAL MEDICINE PURPOSES

(75) Inventors: Alessio Burlon, Belluno (IT); Sergio Badocco, Motta di Livenza (IT); Lorenzo Secco, Treviso (IT); Gaetano Rizzo, Bari (IT)

(73) Assignee: Teleios S.R.L., Bari (IT)

( * ) Notice: Subject to any disclaimer, the term of this patent is extended or adjusted under 35 U.S.C. 154(b) by 360 days.

(21) Appl. No.: 13/877,820

(22) PCT Filed: Sep. 27, 2011

(86) PCT No.: PCT/EP2011/066790
§ 371 (c)(1),
(2), (4) Date: Jun. 18, 2013

(87) PCT Pub. No.: WO2012/045616
PCT Pub. Date: Apr. 12, 2012

(65) Prior Publication Data
US 2013/0272572 A1    Oct. 17, 2013

(30) Foreign Application Priority Data
Oct. 8, 2010   (IT) .............................. TV2010A0133

(51) Int. Cl.
*G06K 9/00* (2006.01)
*G06T 7/00* (2006.01)
(Continued)

(52) U.S. Cl.
CPC ................ *G06T 7/0044* (2013.01); *A61B 6/12* (2013.01); *A61B 6/583* (2013.01); *A61B 6/4085* (2013.01); *A61B 2019/5259* (2013.01); *A61B 2019/5265* (2013.01); *A61B 2019/5289* (2013.01);
(Continued)

(58) Field of Classification Search
None
See application file for complete search history.

(56) References Cited

U.S. PATENT DOCUMENTS

2003/0152195 A1* 8/2003 Hebecker ............. A61B 6/4405
378/162
2008/0119712 A1* 5/2008 Lloyd .......................... 600/407
(Continued)

OTHER PUBLICATIONS

Hamming et al. (NPL: "Automatic Image-to-World Registration based on x-ray projections in cone-beam CT guided interventions", Med. Phys. 36, May 2009.*

*Primary Examiner* — Nirav G Patel
*Assistant Examiner* — Oneal R Mistry
(74) *Attorney, Agent, or Firm* — Novak Druce Connolly Bove + Quigg LLP

(57) ABSTRACT

The present invention relates to an apparatus and to a method for mapping a three-dimensional space in medical applications for diagnostic, surgical or interventional medicine purposes. The apparatus and the method according to the invention use acquisition means, capable of recording two-dimensional images of said three-dimensional space from at least a first recording position and from a second recording position, and a reference target, comprising a plurality of marker elements and movable between a first target point and a second target point of said three-dimensional space. A processing unit, adapted to receive data indicative of a first image and of a second image of said three-dimensional space, comprises computerized means adapted to calculate registration data to register the two-dimensional reference systems, used to express the coordinates of the points of said first image and of said second image, with the three-dimensional reference system, defined by the marker elements of said reference target.

24 Claims, 15 Drawing Sheets

(51) Int. Cl.
*A61B 6/00* (2006.01)
*A61B 6/12* (2006.01)
*A61B 19/00* (2006.01)

(52) U.S. Cl.
CPC . *A61B2019/5295* (2013.01); *A61B 2019/5483* (2013.01)

(56) References Cited

U.S. PATENT DOCUMENTS

2009/0118609 A1* 5/2009 Rahn .............................. 600/411
2009/0296893 A1 12/2009 Strobel
2013/0060146 A1* 3/2013 Yang et al. .................... 600/476

* cited by examiner

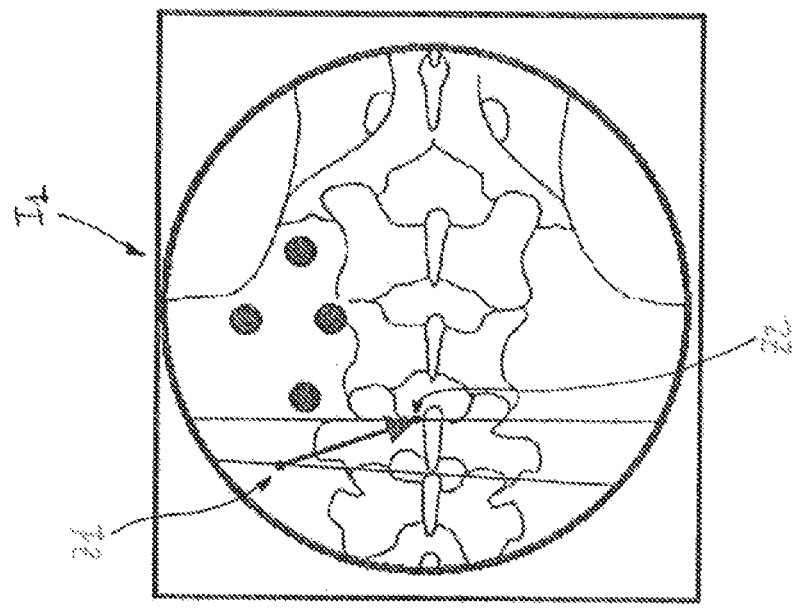
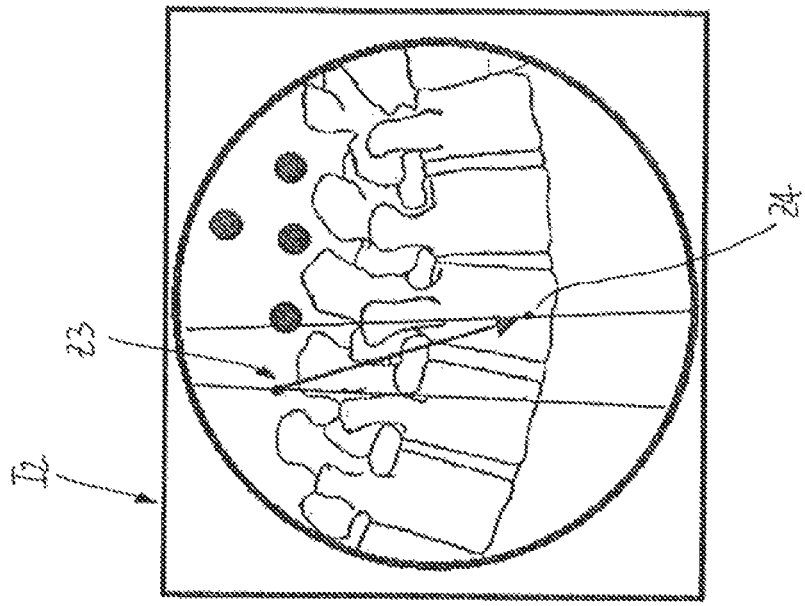
Fig. 14

APPARATUS AND METHOD FOR MAPPING A THREE-DIMENSIONAL SPACE IN MEDICAL APPLICATIONS FOR DIAGNOSTIC, SURGICAL OR INTERVENTIONAL MEDICINE PURPOSES

CROSS REFERENCE TO RELATED APPLICATIONS

This application is a National Phase filing under 35 U.S.C. §371 of PCT/EP2011/066790 filed on Sep. 27, 2011; and this application claims priority to Application No. TV2010A000133 filed in Italy on Oct. 8, 2010 under 35 U.S.C. §119; the entire contents of all are hereby incorporated by reference.

BACKGROUND OF THE INVENTION

The present invention relates to the field of apparatus and methods intended to offer support to a medical operator in the performance of a medical procedure.

More in particular, the present invention relates to an apparatus and to a method for mapping a three-dimensional space in medical applications for diagnostic, surgical or interventional medicine purposes.

It is widely known how, during the performance of a medical procedure, devices are often used that are capable of providing real time images of body parts or internal organs of the patient.

These devices are used, for example, to allow the medical operator to determine optimal operational positioning of medical instruments (e.g. catheters, needles, cutting instruments, etc.) to be used in the medical procedure being performed.

Fluoroscopes are the devices most commonly used to obtain real time images of the patient's internal anatomy, given that they are characterized by relatively limited dimensions, which allow them to be used easily in proximity of the operating field of the medical operator.

A common fluoroscope is illustrated schematically in FIG. 1.

The device (reference 50) comprises a main body 51 and a C-shaped arm 52, movable with six degrees of freedom with respect to the main body. An X-ray source 54 and a fluorescent screen 53 are secured at the opposite end of the arm 52.

To record images of internal organs or body parts, the arm 52 is positioned in such a manner that the patient's body is located in the space between the source and the screen. Typically, the screen 53 is operatively associated with a video camera that allows the images acquired to be reproduced easily on monitors.

Other types of apparatus for real time image acquisition of the patient's anatomy, without the use of ionizing radiation, are available in the state of the art. One example of these is represented by common ultrasound probes.

The images supplied by a fluoroscope or by an ultrasound probe are normally two-dimensional and without absolute references.

Therefore, in order for these images to effectively be of assistance during the medical procedure, it is necessary to map the three-dimensional space in which the patient's body is located, in order to learn the coordinates of its points (and therefore the position of the patient's internal organs and body parts) relative to an absolute reference system.

Some mapping methods, such as the one described in the patent application EP1942662, consist of recording stereoscopic images of the patient's body and establishing a correlation with images of the patient's body, recorded in a pre-operative phase and provided with predefined absolute references. Appropriate image recognition algorithms are used to establish this correlation.

Mapping methods of this type are generally lengthy (requiring over 30 minutes) and must be carried out by specialized personnel, who are normally not part of the medical team.

Moreover, the reliability of these methods is limited, given that often the position of the internal organs of the patient is not the same in the pre-operative phase and during performance of the medical procedure.

Other mapping methods, such as the one described in the U.S. Pat. No. 6,167,292, consist of the use of marker elements rigidly associated with the patient's body, which define a reference system of the three-dimensional space of interest. At the beginning of the medical procedure, the marker elements are "touched" by the operator using a pointer operatively connected to a computerized device which performs matching algorithms to register the three-dimensional reference system, defined by the marker elements, with a known reference system.

Although ensuring high precision, these mapping methods are relatively laborious to use in the field.

It is also inconvenient to secure the marker elements integrally to the patient's body, given that these can in fact undergo shifting due to sudden or imprudent movements of the patient. Moreover, these foreign bodies are a considerable source of discomfort for the patient, who is obliged to suffer their presence for relatively long periods of time.

The patents EP1910040B1 and U.S. Pat. No. 6,349,245B1 describe apparatus for mapping a three-dimensional space wherein a robotic arm, provided with a video camera, is used to automatically detect the position of marker elements, integral with the patient's body. Computerized means calculate the coordinates of the marker elements relative to a known reference system.

Although having the disadvantages linked to the use of marker elements operatively connected to the patient's body, these apparatus allow a reduction of the times required to perform the mapping operations.

However, they are characterized by relatively low precision, given that the position of each marker elements is calculated starting from a detection that is not stereoscopic.

Further mapping methods consist of placing the marker elements on a target in a fixed position, not operatively associated with the patient's body.

These methods consist of recording the target from different positions, recognizing homologous points identifiable in the different views and mapping the three-dimensional space of interest on the basis of geometric relations existing between the homologous points identified.

In order to be performed correctly, these mapping techniques require the images with which the target is recorded to be perfectly isocentric and the target to remain stationary in the space during recording.

Due to the constraints described above, it is difficult to use a common fluoroscope to record images of the three-dimensional space of interest.

In fact, to obtain isocentric images, the fluoroscope must be locked along at least five axes of motion, resulting in a considerable reduction in its operating mobility.

It is therefore extremely difficult, if not impossible, to record images of relatively large three-dimensional spaces.

In the state of the art, computer-assisted navigation devices are available, which are aimed at increasing the visual perception of the medical operator during performance of a medical procedure.

These devices are capable of providing three-dimensional reconstructions of the patient's body parts, which are generally obtained by integrating images acquired in the field with visual structures generated by a computer.

As these navigation systems are generally operatively associated with video camera stereoscopic systems, they can be used to map a three-dimensional space relative to a proper absolute reference system.

The U.S. Pat. No. 7,561,733 describes a mapping method which comprises the use of a pair of video cameras provided with marker elements to record the three-dimensional space of interest. The absolute position of these video cameras is obtained by means of a navigation system. The limitation deriving from use of video cameras which allow only images from outside the patient's body to be acquired is evident.

The U.S. Pat. No. 7,251,522 describes a mapping method which comprises the use of marker elements secured integrally to the end of the C-shaped arm of the fluoroscope, in such a manner as to be framed during recording of the three-dimensional space. The absolute position of the C-shaped arm in the space is obtained by means of a navigation system.

A considerable limitation of this technique consists in the fact that the fluoroscope recordings are themselves subject to non-linear distortions, often caused by external electromagnetic fields. These distortions can cause errors to occur in the mapping operations.

In addition to the drawbacks mentioned, the methods described above also have the disadvantage of being of laborious practical implementation, given that they require the presence of a navigation system. In fact, the use of a navigation system generally constitutes a complex activity, which requires a high level of training and which often must be operated by specialized personnel.

SUMMARY OF THE INVENTION

The main aim of the present invention is to provide an apparatus and a method for mapping a three-dimensional space in medical applications for diagnostic, surgical or interventional medicine purposes which allows the problems described above to be solved.

Within this aim, a further object of the invention is to provide an apparatus and a method for mapping a three-dimensional space which is of easy and rapid practical use.

A further object of the present invention is to provide an apparatus and a method for mapping a three-dimensional space which have a high level of precision and reliability.

A further object of the present invention is to provide an apparatus for mapping a three-dimensional space which has relatively limited dimensions and which can be easily installed in the field.

Another object of the present invention is to provide an apparatus for mapping a three-dimensional space which is easy to produce at industrial level, at competitive costs.

This aim and these objects are achieved, according to the invention, by an apparatus, according to the following claim 1, and by a method, according to the following claim 7.

The apparatus and the method according to the invention allow high precision and reliable mapping of a three-dimensional space used to perform a medical procedure.

The medical operator can learn, in real time, the absolute position of patient's internal organs or body parts, relative to a predefined reference system, starting from two-dimensional images of the operating space of interest, for example obtained by means of a fluoroscope.

This allows, for example, the trajectories along which to move or position any medical instruments to be used to be established with precision.

The apparatus and the method according to the invention are considerably versatile and easy to use, being particularly suitable for mapping three-dimensional spaces which are difficult to access in order to position a reference target.

The apparatus according to the invention is easy and inexpensive to produce at industrial level. It can be easily installed in the field and can be configured physically in a simple and versatile manner, according to requirements.

BRIEF DESCRIPTION OF THE DRAWINGS

Further characteristics and advantages of the present invention will be more apparent with reference to the description given below and to the accompanying figures, provided purely for explanatory and non-limiting purposes, wherein:

FIGS. 13-15 show some steps of a method for determining operational positioning of a medical instrument which uses the method or the apparatus according to the present invention.

DETAILED DESCRIPTION

With reference to the aforesaid figures, the apparatus and the method according to the invention will now be described in detail.

However, before proceeding it is suitable to clarify the meaning of some terms which are repeatedly used to describe the present invention.

The term "three-dimensional space" is intended, within the scope of the present invention, as any operating space of interest for the medical operator. This operating space generally comprises the area in which the body part of the patient who is to undergo the procedure is located.

The expression "mapping a three-dimensional space" is intended, in this context, as the operation (a transformation of the type R2×R2→R3) to establish the coordinates of said three-dimensional space relative to a certain reference system, in such a manner that, from a geometric viewpoint, it is a normed and measurable vector space.

The expression "registering a reference system with another reference system" is intended, in this context, as the operation of determining the geometric relations that link the two reference systems in question.

The term "computerized means" is intended in this context as one or more software programs, codes, modules and/or routines which can be stored on and executed by a processing unit.

The term "interventional medicine" refers to those medical procedures, according to which an intervention on the patient's body is foreseen, without necessarily involving a surgeon.

In a first aspect thereof, the present invention relates to an apparatus 1 for mapping a three-dimensional space 100 in medical applications for diagnostic, surgical or interventional medicine purposes.

According to the invention, the apparatus 1 comprises acquisition means 10 capable of recording two-dimensional images of the three-dimensional space 100.

Figure 1:
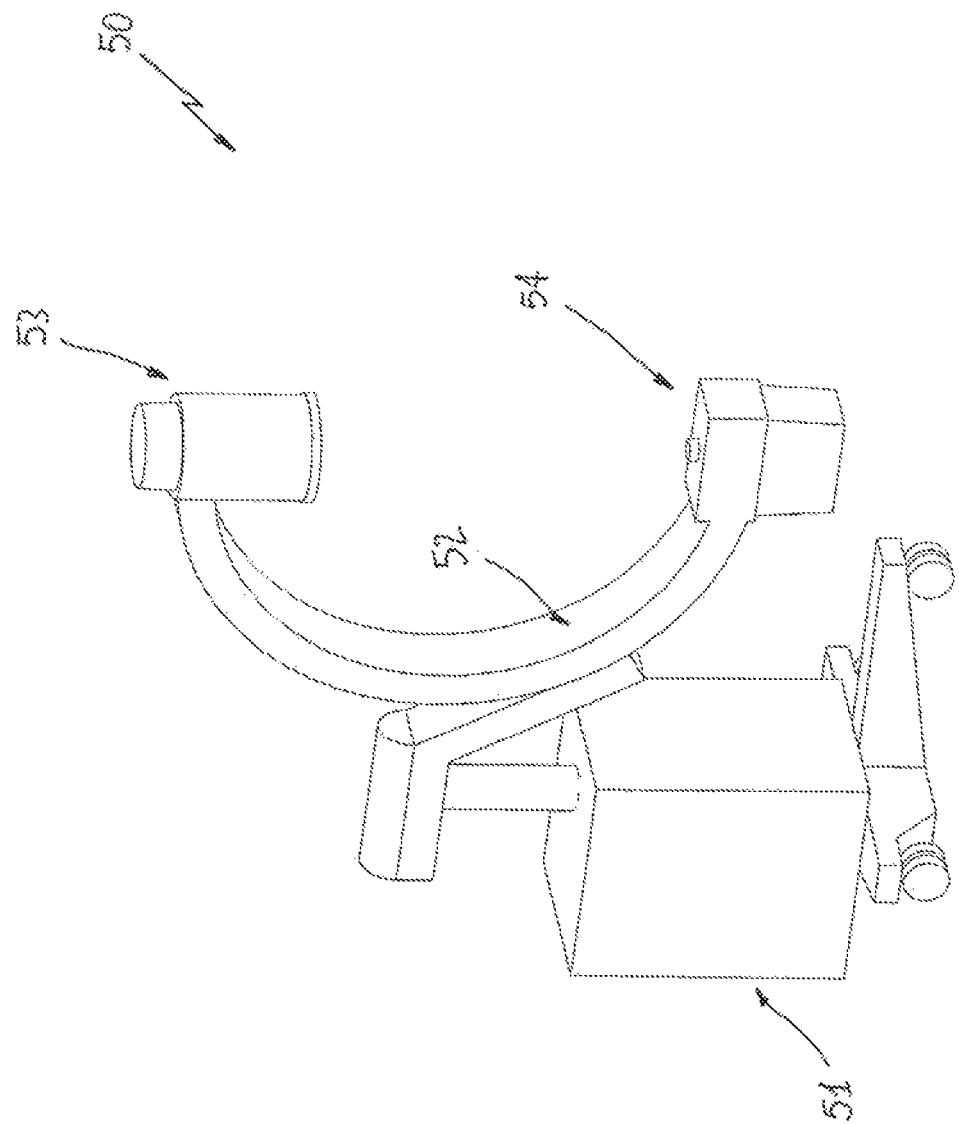
FIG. 1 schematically shows a fluoroscope that can be used in the apparatus and in the method according to the present invention.

The acquisition means 10 can advantageously comprise a fluoroscope of the type described in FIG. 1.

Alternatively, the acquisition means 10 can comprise an ultrasound probe or other devices advantageously adapted to supply images of the patient's internal organs or body parts.

Before use, the acquisition means 10 are preferably subjected to a calibration procedure, given that the images acquired could be subject to distortions, for example caused by the presence of external electromagnetic fields.

In the case of using a fluoroscope, the aforesaid calibration procedure substantially consists of recording a radio-opaque grid comprising an array of holes mutually positioned at predefined distances.

The distorted image is processed in such a manner as to determine a matrix transformation of the type R2→R2 (pixel to pixel) which makes it possible to obtain an image in which the grid appears in its original form. This matrix transformation is therefore used to process each image recorded by the fluoroscope, in such a manner as to correct the distortion thereof.

As shown in FIGS. 5-8, the acquisition means 10 are capable of recording the three-dimensional space 100 from at least a first recording position P1, for example to make an AP (Antero-Posterior) recording of the patient's body, and from a second recording position P2, for example to make an LL (Lateral-Lateral) recording of the patient's body.

The coordinates of the recording positions P1-P2 are not initially known and may be changed from time to time according to the needs.

According to the invention, the apparatus 1 also comprises a reference target 11 (FIG. 4) which comprises a plurality of marker elements $M_1$, $M_2$, $M_3$, $M_4$, produced in such a manner as to be observable by the acquisition means 10 and preferably mounted on a support transparent for the acquisition means 10.

For example, in the case in which a fluoroscope is used to record the three-dimensional space 100, the target 11 can advantageously comprise a support made of radio-transparent material and marker elements constituted by spheres made of radio-opaque material.

The marker elements $M_1$, $M_2$, $M_3$, $M_4$ are mutually positioned in the space according to a predefined geometry, in such a manner as to define a three-dimensional reference system $B_{Rif}$ when the target 11 is located in a first target point B1.

Figure 4:
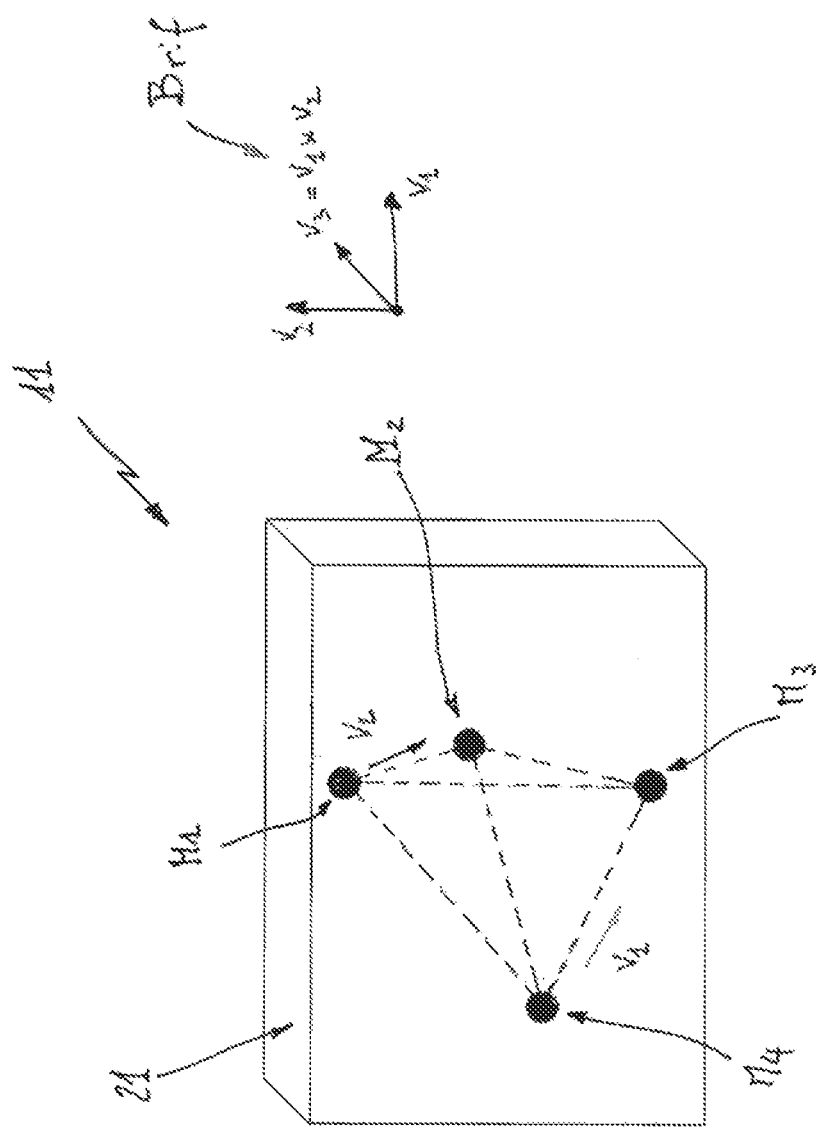
FIG. 4 schematically shows the structure of a reference target that can be used in the apparatus and in the method according to the present invention.
Figure 5:
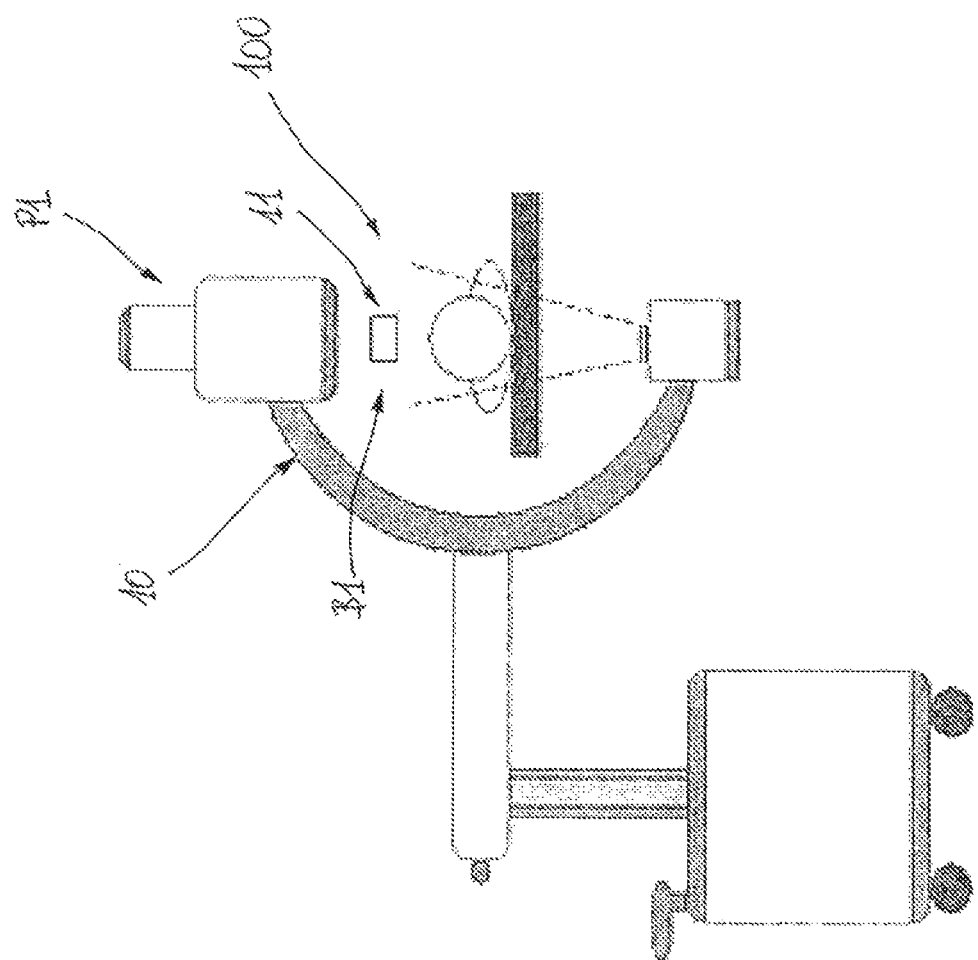
FIGS. 5-12 schematically show the operation and practical implementation of the apparatus and of the method according to the present invention.
Figure 6:
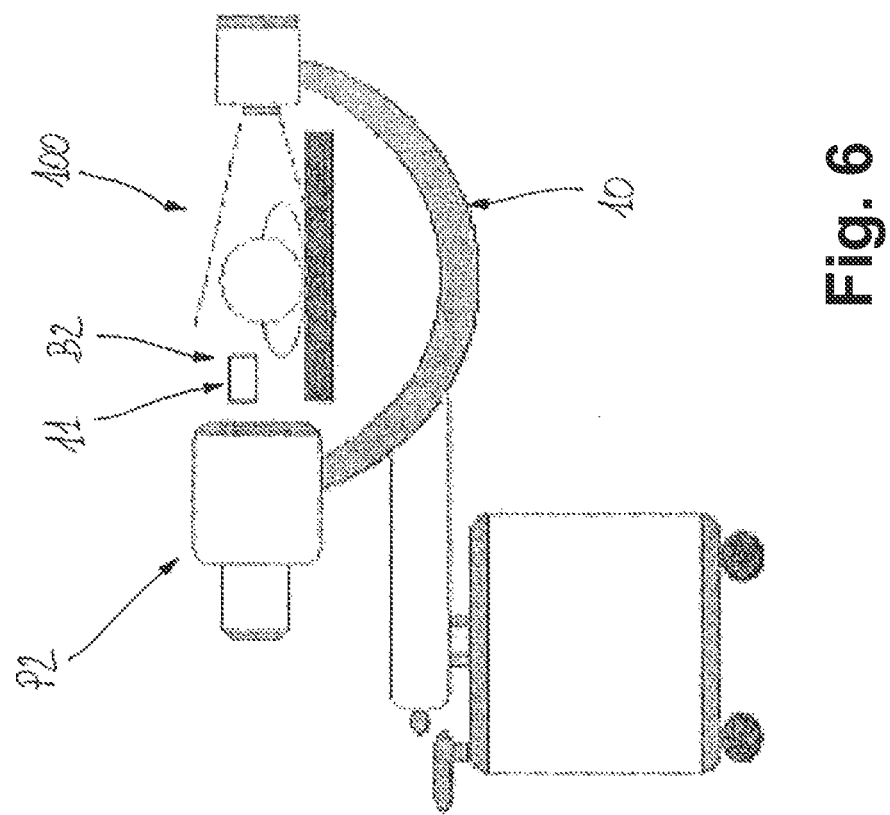

For example, as shown in FIG. 4, the marker elements can be arranged in such a manner as to form an irregular tetrahedron with sides of predefined length and orientation. The combination of direct vectors along the edges of the tetrahedron defines a three-dimensional Cartesian reference system with axes $V_1$, $V_2$, $V_3$.

Obviously, the arrangement and the number of the marker elements can differ from those shown in the figures.

According to the invention, the reference target 11 is movable, in particular at least between the first target point B1 and a second target point B2, in known position relative to the first target point B1.

It is to be noted that, in general, the apparatus 1 thus does not need to know the positions of the target points B1 and B2 but only the relative position of the target point B2 with respect to B1.

Of course, this latter condition is satisfied in case the apparatus knows both the positions of the target points B1 and B2.

Preferably, the apparatus 1 comprises detection means 14 adapted to detect the shift of the target 11 between the target points B1 and B2.

The detection means 14 can, for example, be constituted by the position/motion sensors of a robotic arm 15 (FIG. 2), by the system of stereoscopic video cameras of a navigation system or by a laser detection device of a tracking system.

Alternatively, the movement in the space of the target 11 can take place between predefined target points B1 and B2 or can be carried out with predefined movements, starting from the target point B1.

Preferably, movement of the target 11 is performed by a robotic arm 15 provided with an appropriate flange for mounting the target 11.

However, it is possible to use movement devices of different type, for example manipulators without a motor provided with passive kinematic chains.

The apparatus 1 comprises a processing unit 12, preferably a microprocessor, adapted to receive data indicative of the images of the three-dimensional space 100 recorded by the acquisition means 10.

In particular, the processing unit 12 is capable of receiving data indicative of a first image I1 acquired with the acquisition means 10 located in the first recording position P1.

The image I1 is recorded with the reference target 11 positioned in the first target point B1, in such a manner as to be framed by the acquisition means 10 positioned in the first recording position P1.

Similarly, the processing unit 12 is capable of receiving data indicative of a second image I2 acquired with the acquisition means 10 located in the second recording position P2.

The image I2 is recorded with the target 11 positioned in the second target point B2, in such a manner as to be framed by the acquisition means 10 positioned in the second recording position P2.

Figure 7:
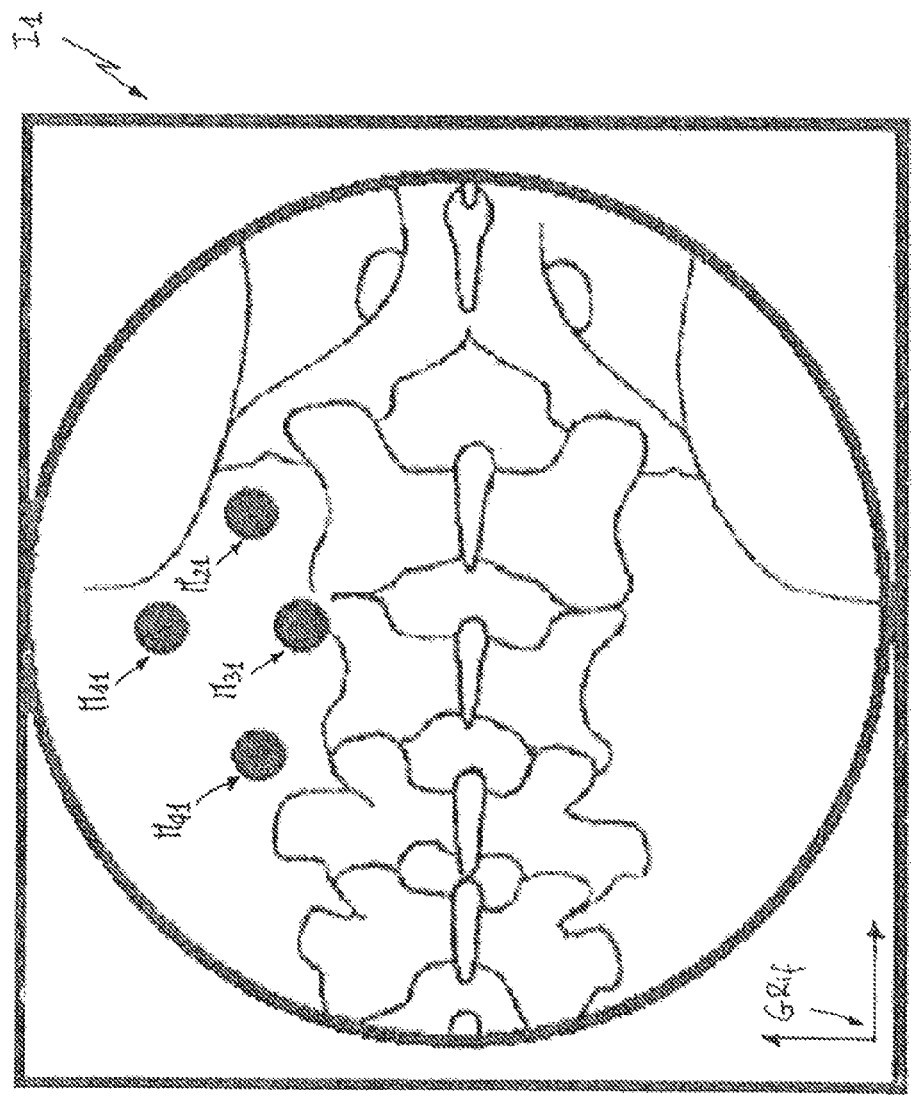
Figure 8:
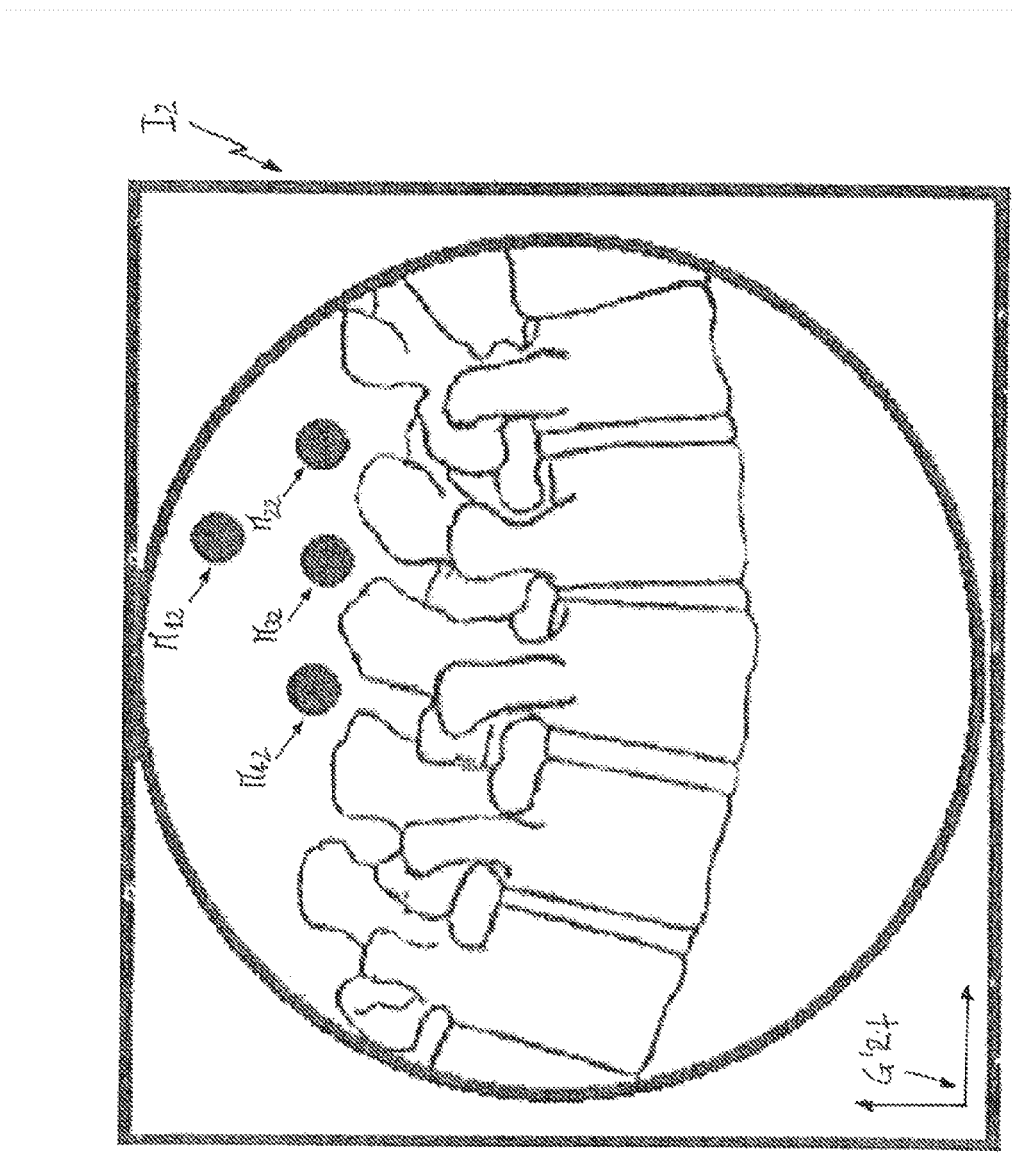

FIGS. 7-8 show, purely by way of example, the images I1 and I2 of a three-dimensional operating space in which a tract of the spinal column is positioned.

The images I1 and I2 are recorded by means of a fluoroscope, of the type shown in FIG. 1, positioned in position AP and in position LL, respectively.

The outlines of the marker elements $M_1$, $M_2$, $M_3$, $M_4$ of the reference target 11, respectively positioned in two different target points of the three-dimensional space of interest can be seen at the relative projection points, superimposed on the tract of spinal column.

According to the invention, the processing unit 12 comprises computerized means 120 to calculate registration data to register the two-dimensional reference systems $G_{Rif}$ and $G'_{Rif}$ respectively used to express the coordinates of the image I1 and of the image I2, with the three-dimensional reference system $B_{Rif}$, defined by the marker elements $M_1$, $M_2$, $M_3$, $M_4$ of the reference target 11.

Figure 2:
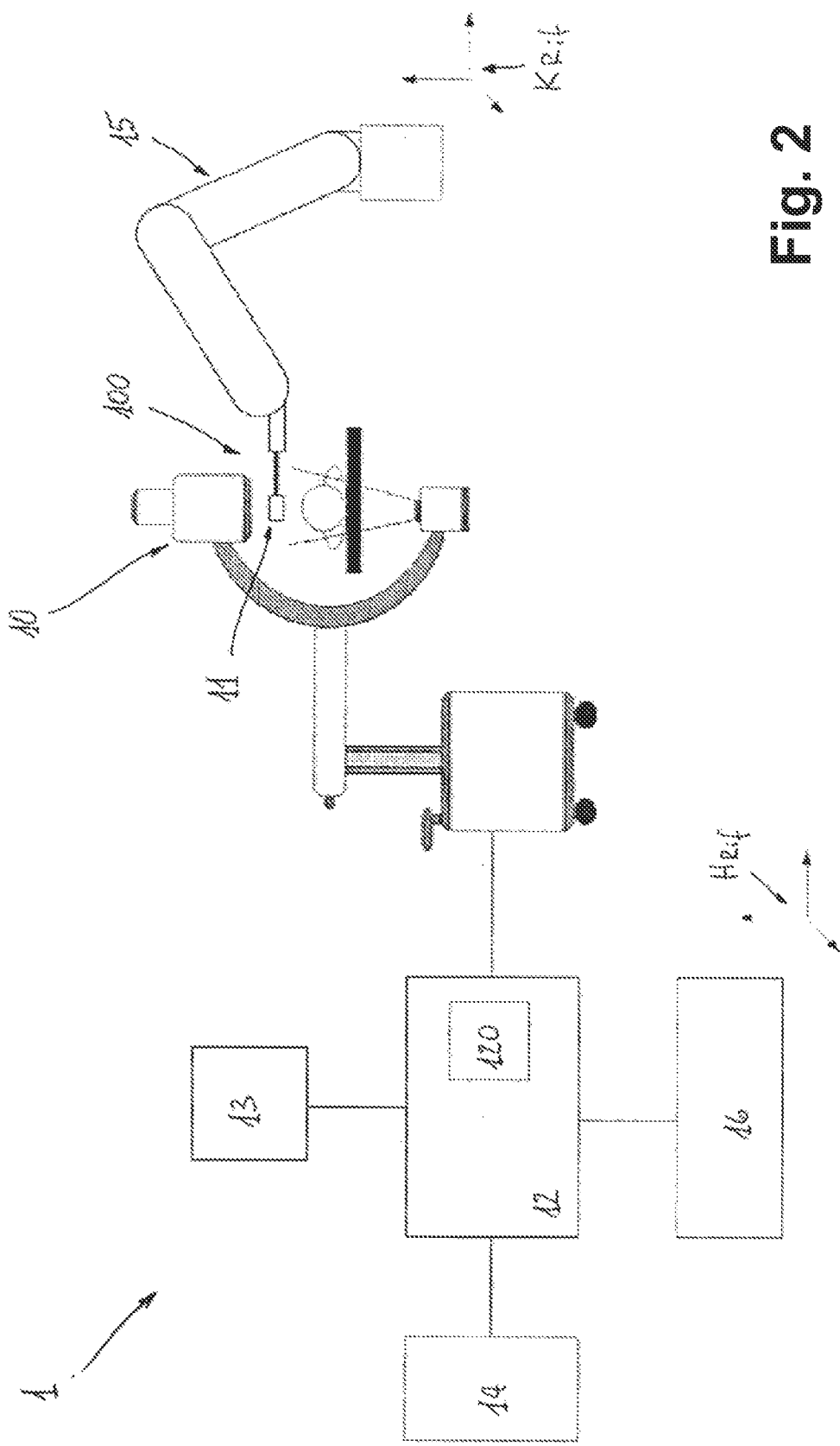
FIG. 2 schematically shows the structure of the apparatus, according to the present invention.

The reference systems $G_{Rif}$ and $G'_{Rif}$ can be, for example, the reference systems used in an appropriate graphic interface 13 of the apparatus 1, by means of which the images I1 and I2 are made available to the medical operator (FIGS. 2, 7-8).

In principle, a same reference system could be used to express the coordinates of the images I1 and I2.

Figure 9:
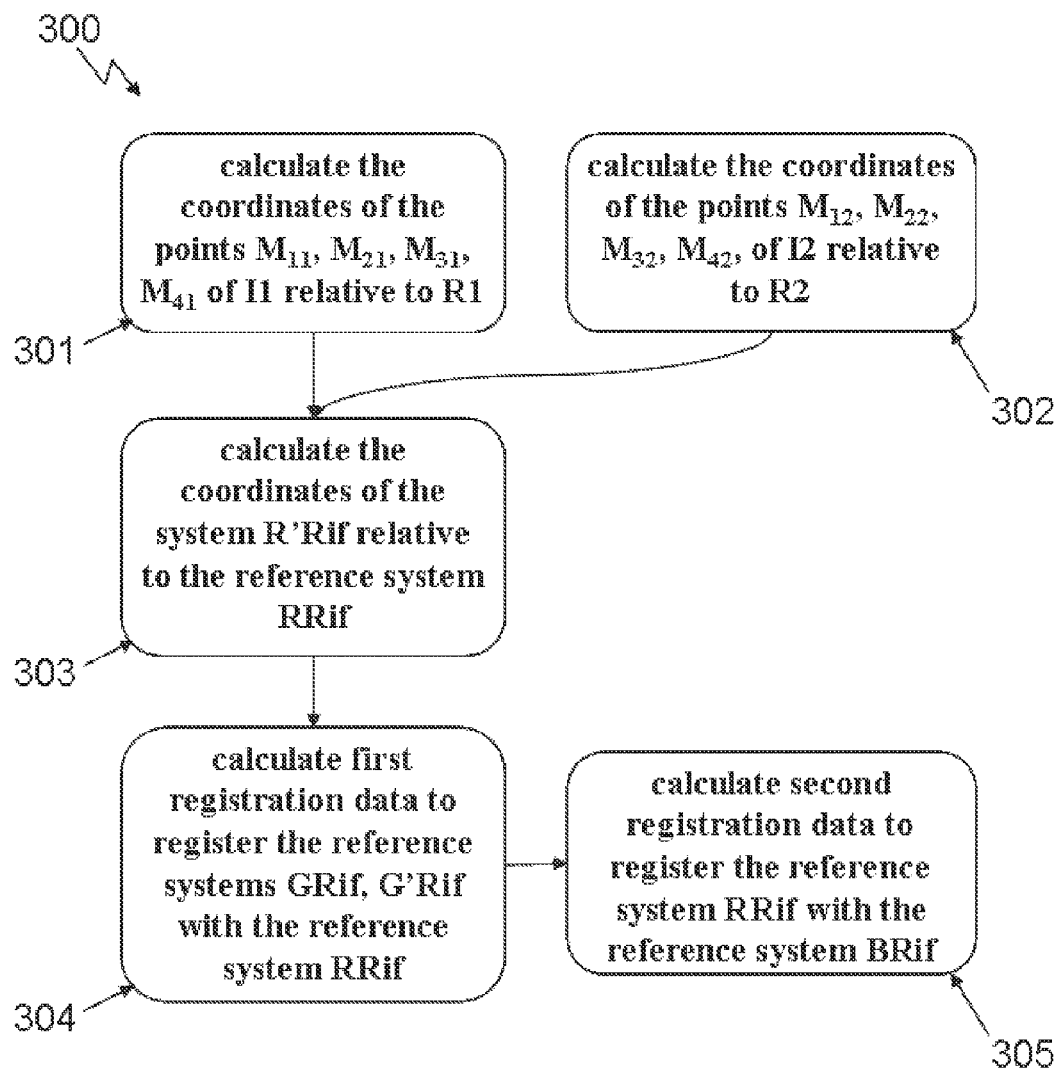

FIG. 9 shows a preferred processing procedure 300 carried out by the computerized means 120 to calculate the registration data to register the reference systems $G_{Rif}$, $G'_{Rif}$ and $B_{Rif}$.

Figure 11:
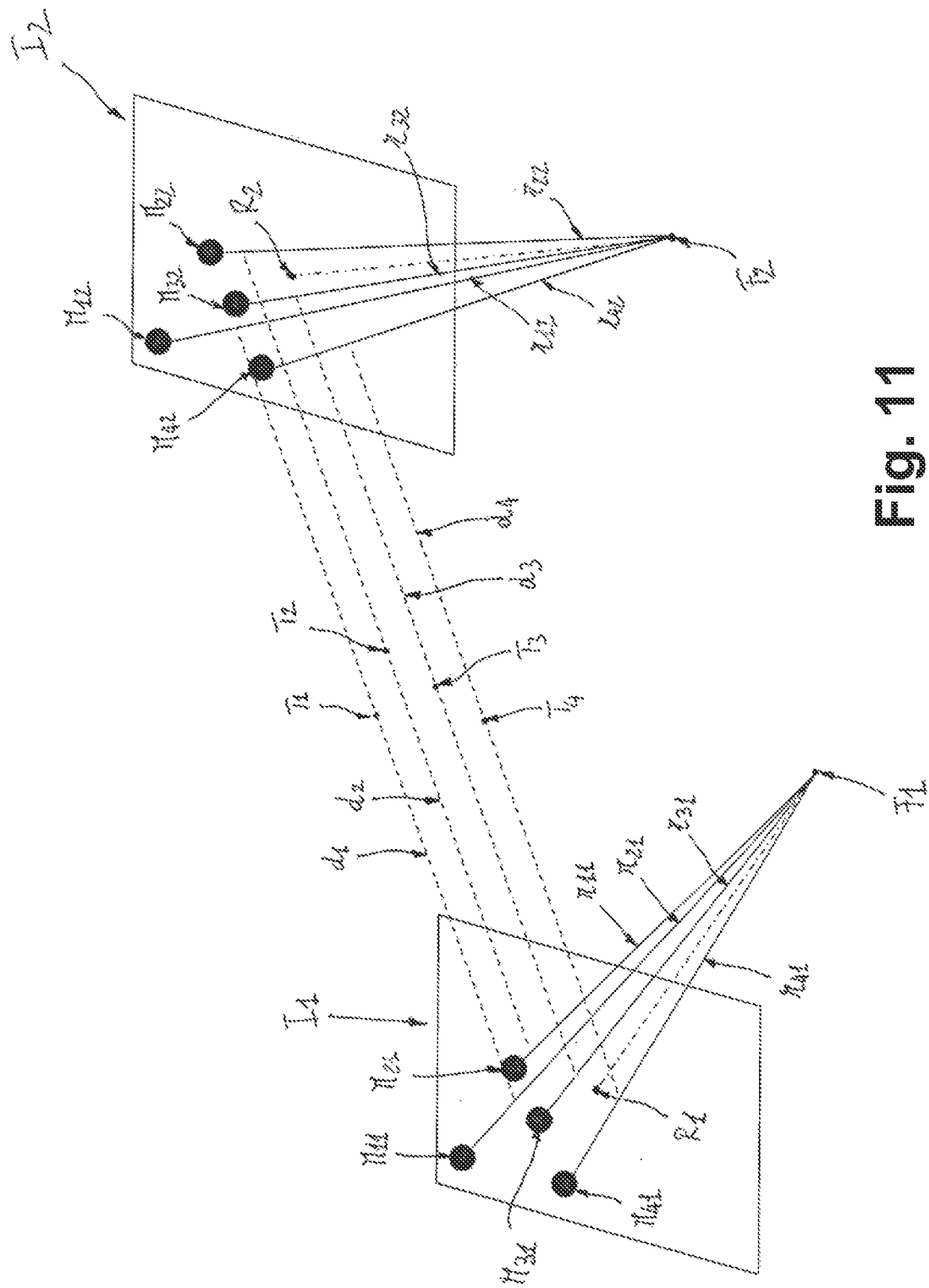

The procedure 300 comprises the step 301 of calculating the coordinates of the projection points $M_{11}$, $M_{21}$, $M_{31}$, $M_{41}$ of the marker elements $M_1$, $M_2$, $M_3$, $M_4$ of the reference target 11 in the first image I1, relative to a first reference point R1 (FIGS. 7 and 11).

The reference point R1 can be the center of the image I1, i.e. the projection of the focal center F1 of the acquisition means 10, positioned in the first recording point P1.

Similarly, the processing procedure 300 comprises the step 302 of calculating the coordinates of the projection points $M_{12}$, $M_{22}$, $M_{32}$, $M_{42}$ of the marker elements of the reference target 11 in the first image I2, relative to a second reference point R2 (FIGS. 8 and 11).

The reference point R2 can in turn be the center of the image I2, i.e. the projection of the focal center F2 of the acquisition means 10, positioned in the second recording point P2.

The processing procedure 300 then comprises the step 303 of calculating the coordinates of a three-dimensional reference system $R'_{Rif}$ having the second reference point R2 as origin, relative to a three-dimensional reference system $R_{Rif}$ having the first reference point R1 as origin.

In other words, the step 303 consists of centering of random Cartesian triads of vectors in R1 and R2, and calculating the coordinates of the triad of vectors centered in R2 relative to the three-dimensional reference system $R_{Rif}$ defined by triad of vectors centered in R1.

Figure 10:
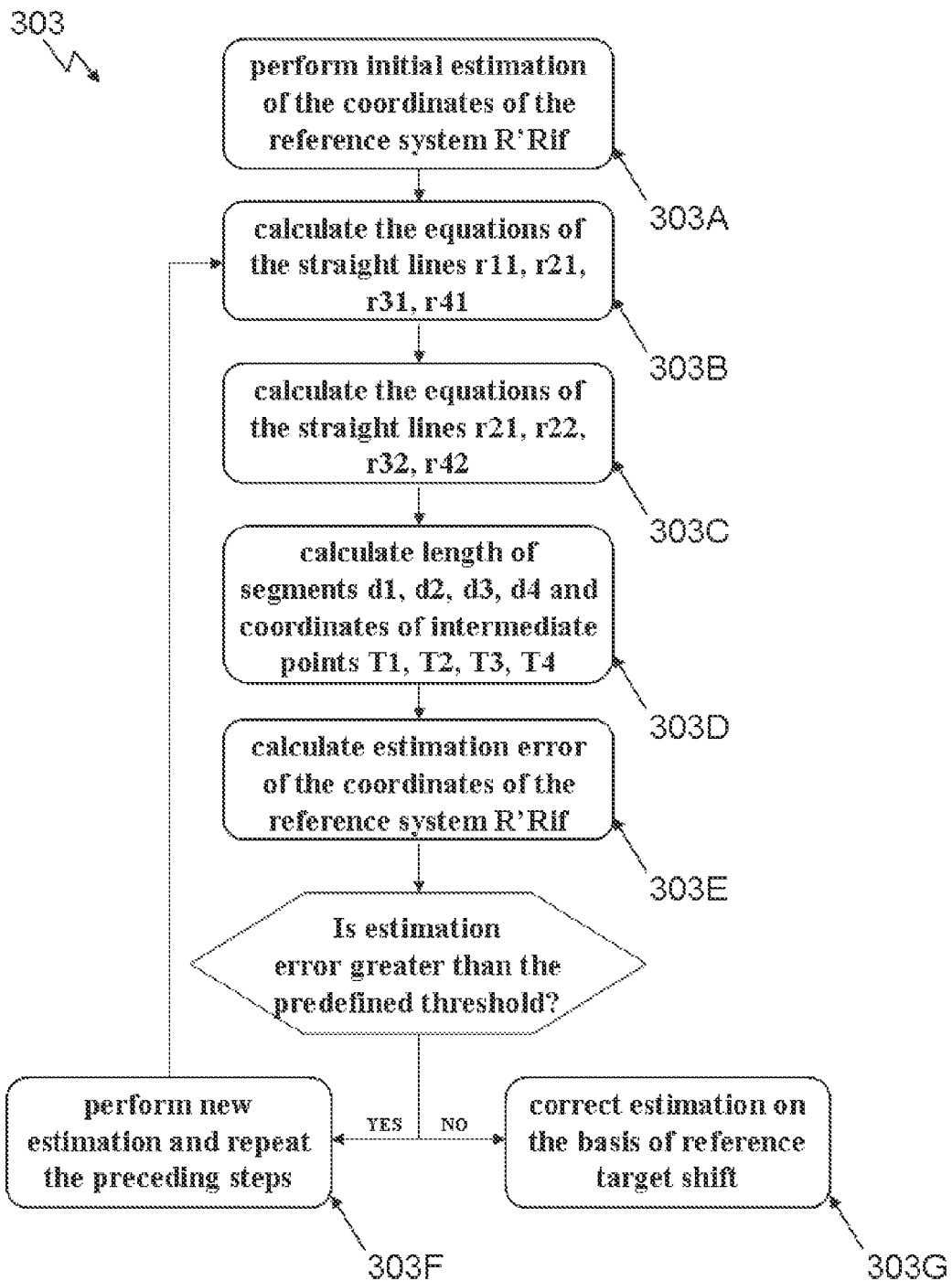

According to a preferred embodiment of the invention, the step 303 consists of performing a recursive estimation process (steps 303A-303F of FIG. 10) of the position of the reference system $R'_{Rif}$ without taking account of the movement of the target 11 between the target points B1 and B2.

For practical implementation of this recursive process it is possible to utilize recursive algorithms for multidimensional optimization.

To establish the geometric relations that link the reference systems $R'_{Rif}$ and $R_{Rif}$ reverse triangulation algorithms which ensure high precision calculations are advantageously used.

In greater detail, the aforesaid recursive estimation process comprises the sequence of steps described in detail below.

Step 303A consists of performing an initial estimation of the position of the reference system $R'_{Rif}$ relative to the three-dimensional reference system $R_{Rif}$. For example, it can be assumed that the position of the reference system $R'_{Rif}$ is linked to that of the reference system of the reference system $R'_{Rif}$ by a predefined relation of roto-translation in the space.

This is followed by step 303B, which consists of calculating the equations of the straight lines $r_{11}$, $r_{21}$, $r_{31}$, $r_{41}$ that join the projection points $M_{11}$, $M_{21}$, $M_{31}$, $M_{41}$ of the marker elements $M_1$, $M_2$, $M_3$ and $M_4$ in the first image I1 with the focal center F1 of the acquisition means 10, positioned in the first recording position P1 (FIG. 11).

Similarly, step 303C consists of calculating the equations of the straight lines $r_{12}$, $r_{22}$, $r_{32}$, $r_{42}$ that join the projection points $M_{12}$, $M_{22}$, $M_{32}$, $M_{42}$ of the marker elements $M_1$, $M_2$, $M_3$ and $M_4$ in the second image I2 with the focal center F2 of the acquisition means 10, positioned in the second recording position P2 (FIG. 11).

Figure 12:
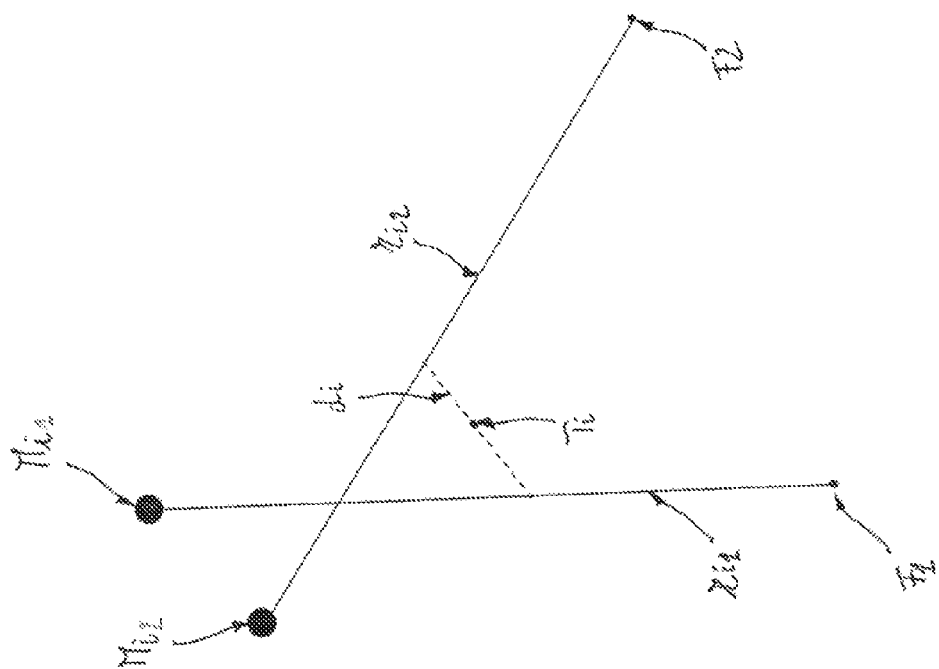
Figure 13:
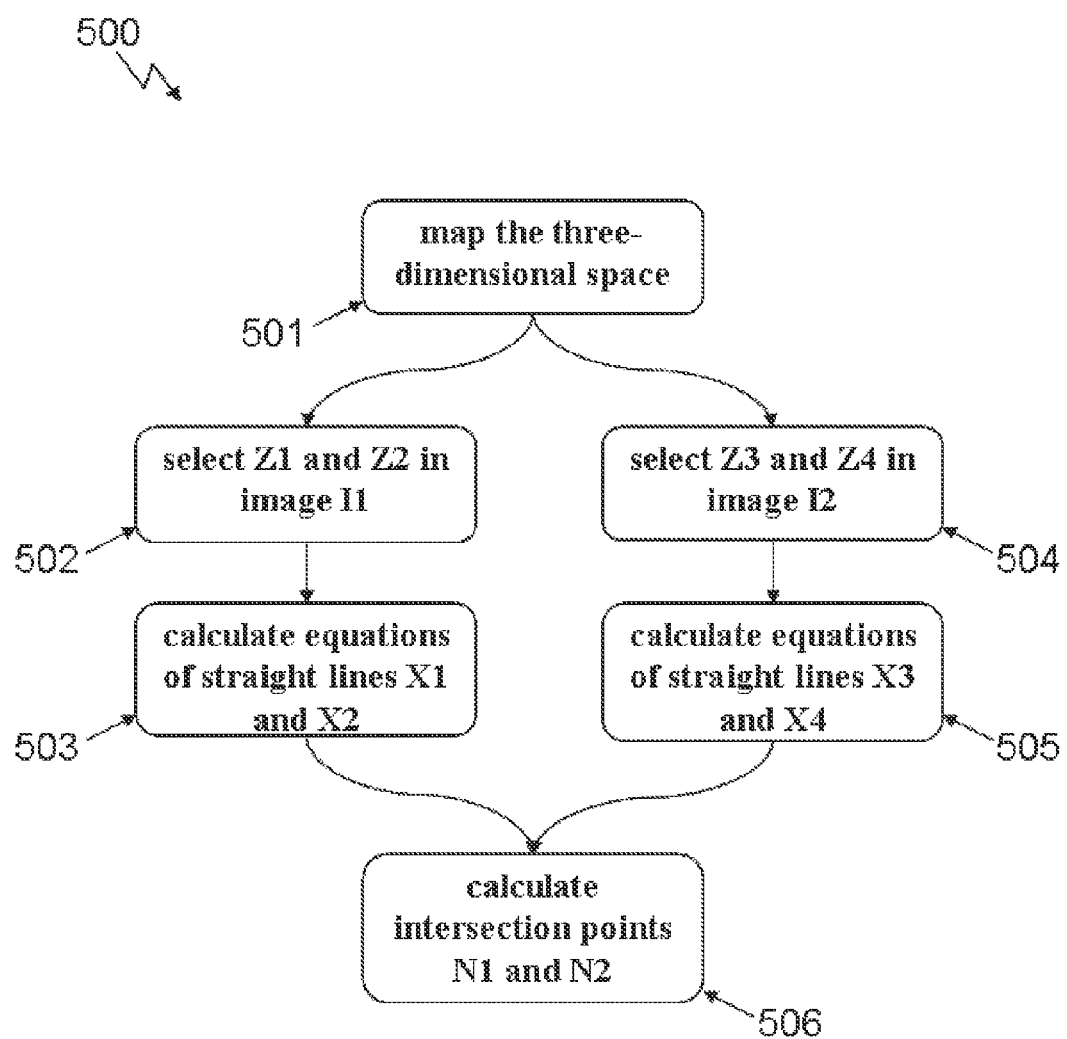
Figure 15:
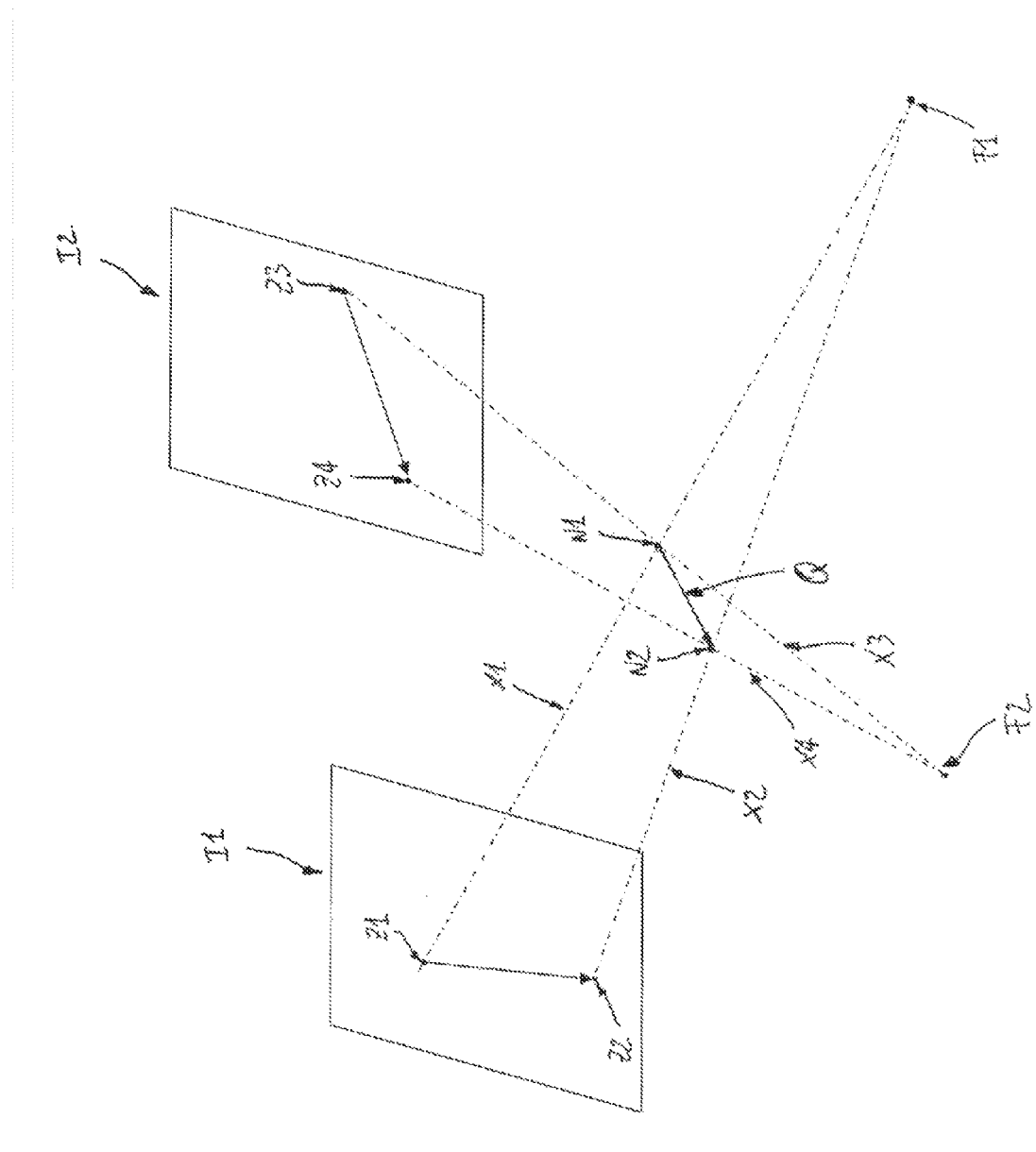

In FIGS. 11-12, it can be observed how, for each marker element Mi (i=1, 2, 3, 4) it is possible to identify a pair of projecting lines ($r_{i1}$, $r_{i2}$), defined herein for convenience as "homologous lines".

If the initial estimation of the coordinates of the reference system $R'_{Rif}$ were exact, the homologous lines ($r_{i1}$, $r_{i2}$) of each marker element Mi (i=1, 2, 3, 4) would intersect one another.

Given that this initial estimation is usually rough, the homologous lines of each marker element do not intersect one another (FIG. 12).

The aforesaid recursive process comprises the step 303 D of calculating, for each pair of homologous lines, data indicative of the coordinates of the intermediate points $T_1$, $T_2$, $T_3$, $T_4$ and of the lengths of the segments $d_1$, $d_2$, $d_3$, $d_4$ which express the minimum distance between the aforesaid homologous lines.

It must be noted how the length of the segments $d_1$, $d_2$, $d_3$, $d_4$ is indicative of the estimation error of the position of the reference system $R'_{Rif}$, while the intermediate points $T_1$, $T_2$, $T_3$, $T_4$ of these segments (for example the median points) can be considered as the real points of intersection of the pairs of homologous lines.

By joining these points it is possible to reconstruct the assumed geometry in the space of the marker elements $M_1$, $M_2$, $M_3$ and $M_4$ and to compare these with the real geometry thereof, in such a manner as to estimate the reconstruction error.

On the basis of the data calculated in the preceding step 303D, the estimation error of the coordinates of the reference system $R'_{Rif}$ is subsequently calculated (step 303E).

If the estimation error is above a predefined threshold, the aforesaid recursive process performs a new estimation of the coordinates of the reference system $R'_{Rif}$, taking account of the estimation error determined in the preceding calculation cycle, and repeating steps 303B-303E described above.

If the estimation error is below the predefined threshold, the calculation procedure of step 303 corrects the estimation thus performed in such a manner as to take account of the shift of the reference target 11 between the target points B1 and B2 (step 303G).

Once step 303 has been completed, the processing procedure 300 consists of calculating first registration data to perform registration of the two-dimensional reference systems $G_{Rif}$ and $G'_{Rif}$ used to express the coordinates of the points of the images I1 and I2, with the three-dimensional reference system $R_{Rif}$ having the first reference point R1 as origin.

Calculation of the coordinates of the reference system $R'_{Rif}$ relative to the three-dimensional reference system $R_{Rif}$ performed in step 303, allows mapping of all the points of the images I1 and I2 relative to the reference system $R_{Rif}$ by means of a matrix transformation of the type R2×R2→R3.

On the other hand, the relations that link the points of the images I1 and I2 to the reference points R1 and R2, respectively, were calculated in steps 301 and 302 of the processing procedure 300.

The processing procedure 300 then comprises the step 305 of calculating second registration data to perform registration of the reference system $R_{Rif}$ with the reference system $B_{Rif}$ defined by the marker elements $M_1$, $M_2$, $M_3$ and $M_4$ of the reference target 11.

Moreover, calculation of the coordinates of the reference system $R'_{Rif}$ relative to the three-dimensional reference system $R_{Rif}$ performed in step 303, allows calculation of the position in the space of the marker elements $M_1$, $M_2$, $M_3$ and $M_4$ relative to the three-dimensional reference system $R_{Rif}$ and consequently determination of the matrix transformation of the type R3→R3 that geometrically links the reference systems $R_{Rif}$ and $B_{Rif}$ to each other.

By composing the matrix transformations calculated in steps 304 and 305, it is possible to establish a matrix transformation of the type R2×R2→R3 which links the reference systems $G_{Rif}$, $G'_{Rif}$ and $B_{Rif}$.

Therefore, the aforesaid first and registration data allow registration of the two-dimensional reference systems $G_{Rif}$ and $G'_{Rif}$ with the three-dimensional reference system $B_{Rif}$.

The three-dimensional space 100 is thus a normed and measurable vector space, whose points are in one-to-one relation with the points of the images I1 and I2.

The coordinates of the points of the three-dimensional space 100 can therefore be learned starting from the images I1 and I2.

To express the coordinates of the reference space 100, a different reference system to the reference system $B_{Rif}$ can be selected, provided that this reference system is in known relation with the reference system $B_{Rif}$.

For example, in the case in which the reference target 11 is moved by a robotic arm, the points of the three-dimensional space 100 could refer to a reference system $K_{Rif}$ used by the control unit of the robotic arm (FIG. 2).

In this case, the processing procedure 300 comprises a further step of calculating the registration data to register the reference system $B_{Rif}$ with the reference system $K_{Rif}$ of the robotic arm. Performance of these calculations is relatively easy, as the target reference 11 is constrained rigidly to the robotic arm.

According to a preferred embodiment, the apparatus 1 can register the two-dimensional reference system $G_{Rif}$ and $G'_{Rif}$ used to express the coordinates of the points I1 and I2 with a three-dimensional reference system $H_{Rif}$ used to express the coordinates of the points of images acquired by means of a tomography scanning apparatus 16, for example a computerized axial tomography or magnetic resonance apparatus (FIG. 2).

In this case, the processing unit 12 receives data indicative of an image of the three-dimensional space 100, acquired by means of a tomography scanning procedure.

Second computerized means (not shown) are advantageously stored in the computerized unit 12 to perform a further processing procedure to calculate registration data to perform registration of the two-dimensional reference systems $G_{Rif}$ and $G'_{Rif}$ with a three-dimensional reference system $H_{Rif}$ used to express the coordinates of the points of the image acquired by means of tomography scanning.

Preferably, this processing procedure consists of identifying at least three homologous points in the images I1 and I2 and in the image acquired by means of tomography scanning, and of calculating a matrix transformation that interrelates the reference systems $G_R$, $G'_{Rif}$ and $H_{Rif}$, on the basis of the arrangement of the aforesaid homologous points.

Figure 3:
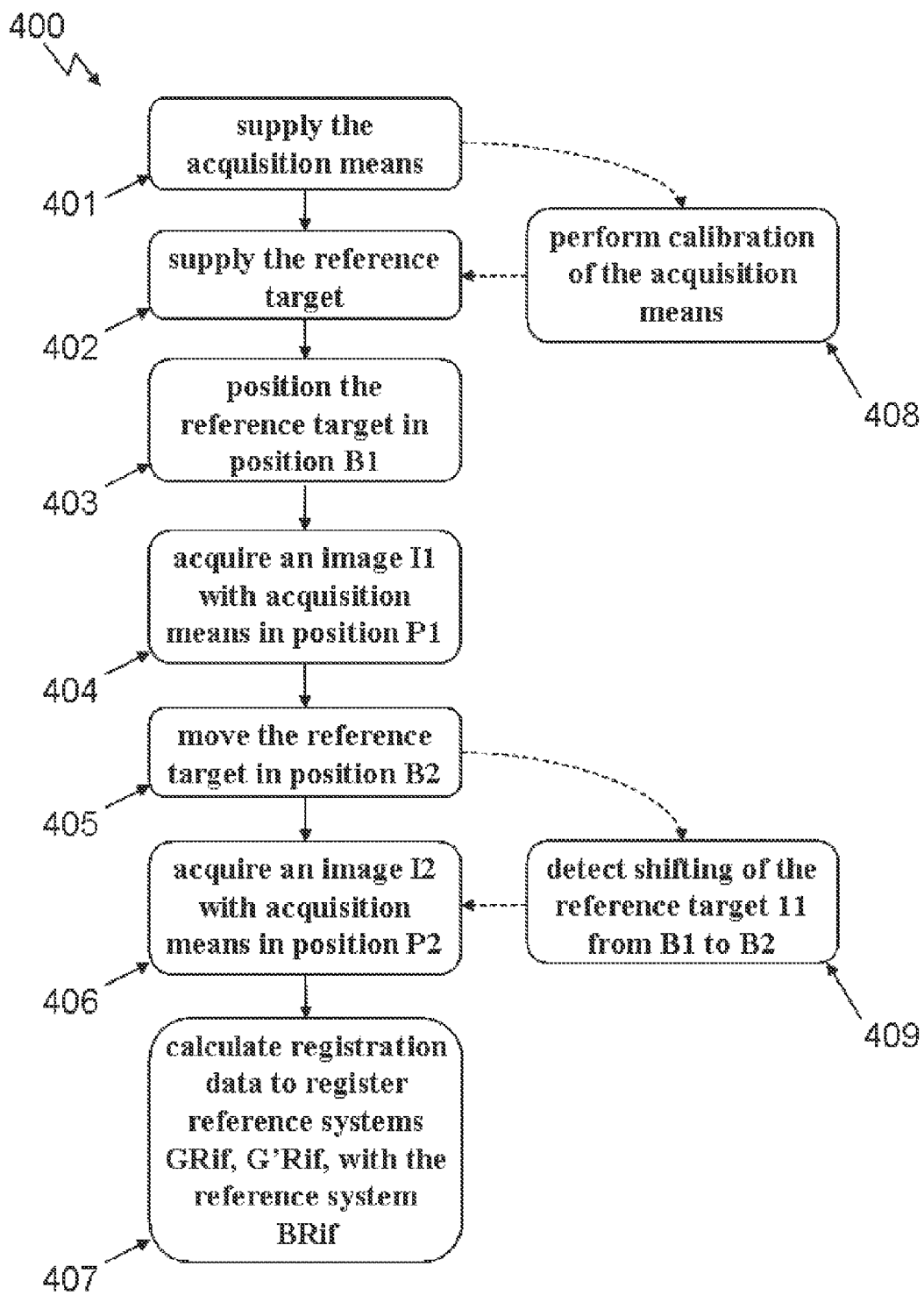
FIG. 3 shows some steps of the method according to the present invention.

As stated, in a further aspect thereof, the present invention also relates to a method 400 for mapping a three-dimensional space in medical applications for diagnostic, surgical or interventional medicine purposes (FIG. 3).

The mapping method 400 comprises a step 401 of providing acquisition means 10 capable of recording two-dimensional images of the three-dimensional space 100, at least from the first recording position P1 and from the second recording position P2, the coordinates of said positions P1 and P2 being not initially known.

It also includes a step 402 of providing the reference target 11 comprising the plurality of marker elements $M_1$, $M_2$, $M_3$, $M_4$ observable by the acquisition means 10, said marker elements being mutually positioned in the space according to a predefined geometry in such a manner as to define the three-dimensional reference system $B_{Rif}$, when the target 11 is positioned in the target point B1.

According to the invention, the target 11 is movable between the target points B1 and B2 of the three-dimensional space 100. The target point B2 is located in a known position relative to the target point B1.

The method 400 then comprises the step 403 of positioning the target 11 in the target point B1, in such a manner that the target 11 is framed by the acquisition means 10 positioned in the first recording position P1, and a subsequent step 404 of acquiring a first image I1 of the three-dimensional space 100 by means of the acquisition means 10 positioned in the first recording position P1.

Once the step 404 has been completed, the method 400 comprises the step 405 of shifting the target 11 to the target point B2, in such a manner that the target 11 is framed by the acquisition means 10, positioned in the second recording position P2.

As stated, positioning/moving of the target 11 can advantageously be performed by a robotic arm or by a passive mechanical device. In principle, however, the target 11 could also be positioned operatively in the target points B1 and B2 manually.

Once the target 11 has been positioned in the target point B2, the method 400 comprises the step 406 of acquiring a second image I2 of the three-dimensional space 100, using the acquisition means 10 in the second recording position P2.

Finally, the mapping method 400 comprises a step 407 of calculating registration data to register the two-dimensional reference systems $G_{Rif}$ and $G'_{Rif}$ used to express the coordinates of the points of said first image I1 and second image I2, with the three-dimensional reference system $B_{Rif}$ defined by the marker elements $M_1$, $M_2$, $M_3$, $M_4$.

According to a preferred embodiment, the aforesaid step 407 of calculating the registration data comprises a sequence of steps similar to that illustrated for the processing procedure 300 described above (FIG. 9).

The step 407 therefore comprises the following steps:
 calculating the coordinates of the projection points $M_{11}$, $M_{21}$, $M_{31}$, $M_{41}$ of the marker elements $M_1$, $M_2$, $M_3$, $M_4$ in the first image I1, relative to the reference point R1 of the image I1; and
 calculating the coordinates of the projection points $M_{12}$, $M_{22}$, $M_{32}$, $M_{42}$ of the marker elements $M_1$, $M_2$, $M_3$, $M_4$ in the second image I2, relative to the second reference point R2 of the image I2; and
 calculating the coordinates of the three-dimensional reference system $R'_{Rif}$ having the second reference point R2 as origin, relative to the three-dimensional reference system $R_{Rif}$ having the first reference point R1 as origin; and
 calculating first registration data to perform registration of the two-dimensional reference systems $G_{Rif}$ and $G'_{Rif}$ with the three-dimensional reference system $R_{Rif}$; and
 calculating second registration data to perform registration of the three-dimensional reference system $R_{Rif}$ with the three-dimensional reference system $B_{Rif}$.

Preferably, the above step of calculating the coordinates of the reference system $R'_{Rif}$ relative to the reference system $R_{Rif}$ comprises a sequence of steps similar to those comprised in step 303 of the processing procedure 300 described above (FIGS. 9-12).

Such a sequence of steps therefore comprises:
 performing an initial estimation of the coordinates of the reference system $R'_{Rif}$; and calculating the equations of the straight lines $r_{11}$, $r_{21}$, $r_{31}$, $r_{41}$ that join the projection points $M_{11}$, $M_{21}$, $M_{31}$, $M_{41}$ in the image I1 with the focal center F1 of the acquisition means 10 positioned in the first recording position P1; and calculating the equations of the straight lines $r_{21}$, $r_{22}$, $r_{32}$, $r_{42}$ that join the projection points $M_{12}$, $M_{22}$, $M_{32}$, $M_{42}$ in the image I2 with the focal center F2 of the acquisition means 10 positioned in the second recording position P2; and for each pair of straight lines referring to a same marker element (homologous lines), calculating data indicative of the coordinates of the intermediate points $T_1$, $T_2$, $T_3$, $T_4$ and of the length of the segments $d_1$, $d_2$, $d_3$, $d_4$ that express the minimum distance between said homologous lines; and calculating the estimation error of the coordinates of the reference system $R'_{Rif}$; and if the estimation error is above a predefined threshold, performing a new estimation of the coordinates of the reference system $R'_{Rif}$ and repeating the steps described above; and correcting the estimation of the coordinates of the reference system $R'_{Rif}$, performed in the preceding steps, as a function of the shift of the reference target 11 between the target points B1 and B2.

Preferably, the method 400 comprises a step 408 of performing a preliminary calibration of the acquisition means 10.

Also preferably, after shifting of the reference target 11 between the target points B1 and B2, the method 400 comprises a step 409 of detecting this shift of the target 11, for example by means of position/movement sensors of the robotic arm 15.

In a further preferred variant, the method 400 also comprises the step (not shown in FIG. 3) of acquiring a third image I3 of the three-dimensional space 100, by means of a tomography scanning procedure, and the step of processing registration data to perform registration of the two-dimensional reference systems $G_{Rif}$ and $G'_{Rif}$, used to express the coordinates of the points of the images I1 and I2, with the three-dimensional reference system $H_{Rif}$ used to express the coordinates of the points of said third image.

As illustrated above, the apparatus and the method for mapping according to the present invention allow a sort of calibration of the three-dimensional space 100 to be performed, using images I1 and I2 of a type similar to those normally used by the medical operator during a medical procedure.

The apparatus 1 is therefore suitable to be easily integrated in an apparatus for determining or performing operational positioning of a medical instrument, for diagnostic, surgical or interventional medicine purposes.

After the three-dimensional space of interest has been mapped, any tracking vector, traced on the image I1 and I2, for example with the assistance of the graphic interface 13, can be transformed in real time into a tracking vector of the three-dimensional space 100.

A method 500 to determine positioning of a medical instrument, for diagnostic, surgical or interventional medicine purposes, in a three-dimensional space, is described below.

The method 500 comprises an initial step 501 of mapping the three-dimensional space of interest by means of the apparatus 1 or the method 400 according to the present invention.

This is followed by a step 502 of selecting a first point Z1 and a second point Z2 in the first image I1, for example using the graphic interface 13 or another graphic interface provided specifically for this purpose.

It is noted how this operation is equivalent to the operation of tracing, in the first image I1, a tracking vector for the medical instrument to be positioned.

The method 500 then comprises a step 503 of calculating the equations of a first straight line X1 and of a second straight line X2 which respectively join the points Z1 and Z2 with the focal center of the acquisition means 10 positioned in the first recording position P1.

In the same way as above, the method 500 comprises a step 504 of selecting a third point Z3 and a fourth point Z4 in the second image I2, thus tracing a tracking vector in the image I2.

This is followed by a step 505 of calculating the equations of a third straight line X3 and a fourth straight line X4 that respectively join the third point Z3 and the fourth point Z4, selected in the image I2, with the focal center F2 of the acquisition means 10, positioned in the second recording position P2.

Finally, the method 500 comprises a step 506 of calculating a first intersection point N1 between the straight lines X1 and X3 and a second intersection point N2 between the straight line X2 and the straight line X4.

The intersection points N1 and N2 constitute the ends of a tracking vector Q in the three-dimensional space 100 of interest. The coordinates of the tracking vector Z can be used to perform tracking of the medical instrument, for example by means of a robotic arm.

The steps 503, 505 and 506, which use direct triangulation algorithms, can advantageously be performed automatically by third computerized means (not shown), for example appropriately stored in the processing unit 12.

It has been seen in practice how with the apparatus and the method according to the present invention the objects set forth are achieved.

The apparatus and the method according to the present invention are considerably simple and practical to use. The times required to learn how to use them are relatively short and they do not require to be operated by specialized personnel.

The apparatus and the method, according to the invention, allow to mapping the operative field of the medical operator without the need of establishing a contact between the target 11 and the patient's body and without having an a priori knowledge of the coordinates of the recording points P1 and P2.

These features make the apparatus and the method, according to the invention, considerably versatile and flexible in use.

Mapping of the three-dimensional space is performed in a manner that does not depend on the type and configuration of this latter and on the type of medical procedure to be performed.

The patient is not subjected to further discomfort, given that the reference target does not require to be secured integrally to the patient's body.

The reference target is movable and can be appropriately positioned according to the requirements of the medical procedure being performed. This allows the best use to be made of the operating mobility of the acquisition means, particularly in the case in which a fluoroscope is used, and consequently in which relatively large operating spaces are mapped.

As has been seen, to calculate the registration data of the reference system, the apparatus and the method according to the invention advantageously use calculation processes of the stereoscopic triangulation type. This allows a high level of precision and reliability to be achieved in mapping of the three-dimensional space.

The apparatus according to the invention itself constitutes a real time viewing system of the patient's internal organs and body parts. By means of the graphic interface, the medical operator can in fact view, in real time, the patient's anatomy instead of virtual reconstructions of this latter.

Moreover, the apparatus according to the invention can be easily integrated in/interfaced with tomography scanning apparatus, thereby allowing the medical operator to acquire more detailed information on the patient's anatomy.

The apparatus, according to the invention, is also easy to integrate in apparatus to provide operating support during performance of the medical procedure, for example in apparatus to determine or perform tracking of medical instruments.

The medical operator can use, directly, the graphic interface of the apparatus according to the present invention to study the position of the patient's internal organs or body parts, to trace tracking vectors and define the operating trajectories of medical instruments for diagnostic, surgical or interventional purposes.

The apparatus according to the invention is characterized by relatively limited dimensions and is easy to install in proximity of the operating field of the medical operator. It can be configured in a simple and versatile manner, according to requirements.

Finally, it has been shown how the apparatus according to the invention can be easily produced at industrial level, at competitive costs.

The invention claimed is:

1. An apparatus for mapping a three-dimensional space in medical applications for diagnostic, surgical or interventional medicine purposes, wherein it comprises:
    acquisition means capable of recording two-dimensional images of said three-dimensional space from at least a first recording position and a second recording position, the coordinates of said first and second recording positions being changeable from time to time; and
    a reference target element comprising a plurality of marker elements ($M_1$, $M_2$, $M_3$, $M_4$), observable by said acquisition means, and a support, transparent for said acquisition means, on which said marker elements are mounted, the reference target element being movable between a first target point and a second target point of said three-dimensional space, said second target point being located in known position relative to said first target point, said marker elements being mutually positioned according to a predefined geometry, in such a manner as to define a three-dimensional reference system ($B_{Rif}$), when said reference target element is positioned in said first target point; and
    a processing unit adapted to receive data indicative of a first image and of a second image of said three-dimensional space, said first image being acquired by said acquisition means in said first recording position with said reference target element positioned in said first target point in such a manner as to be framed by said acquisition means in said first recording position, said second image being acquired by said acquisition means in said second recording position with said reference target element shifted in said second target point in such a manner as to be framed by said acquisition means in said second recording position, said processing unit comprising computerized means adapted to calculate registration data to register the two-dimensional reference systems ($G_{Rif}$, $G'_{Rif}$), used to express the coordinates of the points of said first image and of said second image, with the three-dimensional reference system ($B_{Rif}$), defined by the marker elements of said reference target element.

2. The apparatus according to claim 1, wherein it comprises detection means to detect the shift of said reference target element from said first target point to said second target point.

3. The apparatus according to claim 2, wherein it comprises a robotic arm to position and move said reference target element in the space.

4. The apparatus according to claim 2, wherein said acquisition means comprise an acquisition device movable between said first recording position and said second recording position.

5. The apparatus according to claim 2, wherein said computerized means perform a processing procedure that comprises the following steps:
    calculating the coordinates of the projection points ($M_{11}$, $M_{21}$, $M_{31}$, $M_{41}$) of the marker elements of said reference target element in said first image (I1), relative to a first reference point of said first image; and
    calculating the coordinates of the projection points ($M_{12}$, $M_{22}$, $M_{32}$, $M_{42}$) of the marker elements of said reference target element in said second image (I2), relative to a second reference point of said second image; and
    calculating the coordinates of a three-dimensional reference system ($R'_{Rif}$), having said second reference point as origin, relative to a three-dimensional reference system ($R_{Rif}$), having said first reference point (R1) as origin; and
    calculating first registration data to perform registration of the two-dimensional reference systems ($G_{Rif}$, $G'_{Rif}$), used to express the coordinates of the points of said first image and of said second image, with the three-dimensional reference system ($R_{Rif}$), having said first reference point (R1) as origin; and
    calculating second registration data to perform registration of the three-dimensional reference system ($R_{Rif}$), having said first reference point as origin, with the three-dimensional reference system ($B_{Rif}$), defined by the marker elements of said reference target element.

6. An apparatus for determining or performing operational positioning of a medical instrument, for diagnostic, surgical or interventional medicine purposes, wherein it comprises an apparatus for mapping a three-dimensional space according to claim 2.

7. The apparatus according to claim 1, wherein it comprises a robotic arm to position and move said reference target element in the space.

8. The apparatus according to claim 7, wherein said acquisition means comprise an acquisition device movable between said first recording position and said second recording position.

9. The apparatus according to claim 7, wherein said computerized means perform a processing procedure that comprises the following steps:
    calculating the coordinates of the projection points ($M_{11}$, $M_{21}$, $M_{31}$, $M_{41}$) of the marker elements of said reference target element in said first image (I1), relative to a first reference point of said first image; and
    calculating the coordinates of the projection points ($M_{12}$, $M_{22}$, $M_{32}$, $M_{42}$) of the marker elements of said reference target element in said second image (I2), relative to a second reference point of said second image; and calculating the coordinates of a three-dimensional reference system ($R'_{Rif}$), having said second reference point as origin, relative to a three-dimensional reference system ($R_{Rif}$), having said first reference point (R1) as origin; and calculating first registration data to perform registration of the two-dimensional reference systems ($G_{Rif}$, $G'_{Rif}$), used to express the coordinates of the points of said first image and of said second image, with the three-dimensional reference system ($R_{Rif}$), having said first reference point (R1) as origin; and calculating second registration data to perform registration of the three-dimensional reference system ($R_{Rif}$), having said first reference point as origin, with the three-dimensional reference system ($B_{Rif}$), defined by the marker elements of said reference target element.

10. An apparatus for determining or performing operational positioning of a medical instrument, for diagnostic, surgical or interventional medicine purposes, wherein it comprises an apparatus for mapping a three-dimensional space according to claim 7.

11. The apparatus according to claim 1, wherein said acquisition means comprise an acquisition device movable between said first recording position (P1) and said second recording position.

12. The apparatus according to claim 11, wherein said computerized means perform a processing procedure that comprises the following steps:

calculating the coordinates of the projection points ($M_{11}$, $M_{21}$, $M_{31}$, $M_{41}$) of the marker elements of said reference target element in said first image (I1), relative to a first reference point of said first image; and calculating the coordinates of the projection points ($M_{12}$, $M_{22}$, $M_{32}$, $M_{42}$) of the marker elements of said reference target element in said second image (I2), relative to a second reference point of said second image; and calculating the coordinates of a three-dimensional reference system ($R'_{Rif}$), having said second reference point as origin, relative to a three-dimensional reference system ($R_{Rif}$), having said first reference point (R1) as origin; and calculating first registration data to perform registration of the two-dimensional reference systems ($G_{Rif}$, $G'_{Rif}$), used to express the coordinates of the points of said first image and of said second image, with the three-dimensional reference system ($R_{Rif}$), having said first reference point (R1) as origin; and calculating second registration data to perform registration of the three-dimensional reference system ($R_{Rif}$), having said first reference point as origin, with the three-dimensional reference system ($B_{Rif}$), defined by the marker elements of said reference target element.

13. An apparatus for determining or performing operational positioning of a medical instrument, for diagnostic, surgical or interventional medicine purposes, wherein it comprises an apparatus for mapping a three-dimensional space according to claim 11.

14. The apparatus according to claim 1, wherein said computerized means perform a processing procedure that comprises the following steps:

calculating the coordinates of the projection points ($M_{11}$, $M_{21}$, $M_{31}$, $M_{41}$) of the marker elements of said reference target element in said first image (I1), relative to a first reference point of said first image; and calculating the coordinates of the projection points ($M_{12}$, $M_{22}$, $M_{32}$, $M_{42}$) of the marker elements of said reference target element in said second image (I2), relative to a second reference point of said second image; and calculating the coordinates of a three-dimensional reference system ($R'_{Rif}$), having said second reference point as origin, relative to a three-dimensional reference system ($R_{Rif}$), having said first reference point (R1) as origin; and calculating first registration data to perform registration of the two-dimensional reference systems ($G_{Rif}$, $G'_{Rif}$), used to express the coordinates of the points of said first image and of said second image, with the three-dimensional reference system ($R_{Rif}$), having said first reference point (R1) as origin; and calculating second registration data to perform registration of the three-dimensional reference system ($R_{Rif}$), having said first reference point as origin, with the three-dimensional reference system ($B_{Rif}$), defined by the marker elements of said reference target element.

15. An apparatus for determining or performing operational positioning of a medical instrument, for diagnostic, surgical or interventional medicine purposes, wherein it comprises an apparatus for mapping a three-dimensional space according to claim 1.

16. The apparatus of claim 1, wherein the predefined geometry is a fixed arrangement of the marker elements.

17. The apparatus of claim 1, wherein the predefined geometry is a tetrahedron.

18. A method for mapping a three-dimensional space in medical applications for diagnostic, surgical or interventional medicine purposes, wherein the method comprises:

providing acquisition means capable of recording two-dimensional images of said three-dimensional space from at least a first recording position and the second recording position (P2), the coordinates of said first and second recording positions being not known; and providing a reference target element comprising a plurality of marker elements ($M_1$, $M_2$, $M_3$, $M_4$), observable by said acquisition means, and a support, transparent for said acquisition means, on which said marker elements are mounted, the reference target element being movable between a first target point and a second target point of said three-dimensional space, said second target point being located in known position relative to said first target point, said marker elements being mutually positioned according to a predefined geometry in such a manner as to define the three-dimensional reference system ($B_{Rif}$), when said reference target element is positioned in said first target point; and positioning said reference target elemenet in said first target point, in such a manner that said reference target element is framed by said acquisition means in said first recording position; and acquiring a first image of said three-dimensional space using said acquisition means in said first recording position; and shifting said reference target element in said second target point in such a manner that said reference target element is framed by said acquisition means in said second recording position; and acquiring a second image of said three-dimensional space using said acquisition means in said second recording position; and calculating registration data to register the two-dimensional reference systems ($G_{Rif}$, $G'_{Rif}$) used to express the coordinates of the points of said first image and said second image, with the three-dimensional reference system ($B_{Rif}$), defined by the marker elements of said reference target element.

19. The method according to claim 18, wherein it comprises a step of detecting the shift of said reference target element from said first target point to said second target point.

20. The method according to claim 18, wherein it comprises a step of performing a preliminary calibration of said acquisition means.

21. The method according to claim 18, wherein said step of calculating the registration data to register the two-dimensional reference systems ($G_{Rif}$, $G'_{Rif}$) with the three-dimensional reference system ($B_{Rif}$) comprises the following steps:

calculating the coordinates of the projection points ($M_{11}$, $M_{21}$, $M_{31}$, $M_{41}$) of the marker elements of said reference target element in said first image, relative to a first reference point of said first image; and calculating the coordinates of the projection points ($M_{12}$, $M_{22}$, $M_{32}$, $M_{42}$) of the marker elements of said reference target element in said second image, relative to a second reference point of said second image; and calculating the coordinates of a three-dimensional reference system ($R'_{Rif}$), having said second reference point as origin, relative to a three-dimensional reference system ($R_{Rif}$) having said first reference point as origin; and calculating first registration data to perform registration of the two-dimensional reference systems ($G_{Rif}$, $G'_{Rif}$) used to express the coordinates of the points of said first image and of said second image, with the three-dimensional reference system ($R_{Rif}$), having said first reference point as origin; and calculating second registration data to perform registration of the three-dimensional reference system ($R_{Rif}$), having said first reference point (R1) as origin, with the three-dimensional reference system ($B_{Rif}$), defined by the marker elements of said at least one reference target element.

22. A method for determining operational positioning of a medical instrument, for diagnostic, surgical or interventional medicine purposes, in a three-dimensional space wherein it comprises a step of mapping said three-dimensional space by means of a method according to claim 18.

23. The method of claim 18, wherein the predefined geometry is a fixed arrangement of the marker elements.

24. The method of claim 18, wherein the predefined geometry is a tetrahedron.

* * * * *